United States Patent [19]

Hanson

[11] Patent Number: 5,188,121
[45] Date of Patent: Feb. 23, 1993

[54] RANGE OF MOTION INSTRUMENTS FOR THE SPINE

[76] Inventor: Gordon N. Hanson, 958 Lydia Dr., Roseville, Minn. 55113

[21] Appl. No.: 629,232

[22] Filed: Dec. 18, 1990

[51] Int. Cl.$^5$ .............................................. A61B 5/103
[52] U.S. Cl. .................... 128/781; 128/782; 33/512
[58] Field of Search .................. 128/774, 781, 782; 33/511, 512, 343, 347, 351, 352, 538, 534, 515, DIG. 1, DIG. 12; 600/15

[56] References Cited

U.S. PATENT DOCUMENTS

| | | | |
|---|---|---|---|
| 2,532,915 | 12/1950 | Horner | 128/2 |
| 2,565,381 | 8/1951 | Leighton | 128/782 |
| 2,775,040 | 12/1956 | Leff | 33/512 |
| 3,070,887 | 1/1963 | Olsen | 33/343 |
| 3,109,242 | 12/1963 | Nyitrai | 33/538 |
| 3,921,620 | 11/1975 | Nakayama | 128/1.3 |
| 3,943,912 | 3/1976 | Nakayama | 128/1.3 |
| 4,108,164 | 8/1978 | Hall, Sr. | 128/25 |
| 4,444,204 | 4/1984 | Bryant et al. | 128/781 |
| 4,480,596 | 11/1984 | Shumiyashu | 600/15 |
| 4,485,825 | 12/1984 | Domján et al. | 128/774 |
| 4,587,956 | 5/1986 | Griffin et al. | 128/1.3 |
| 4,655,227 | 4/1987 | Gracovetsky | 128/781 |
| 4,665,928 | 5/1987 | Linial et al. | 128/782 |
| 4,730,625 | 3/1988 | Fraser et al. | 128/781 |
| 4,777,965 | 10/1988 | Allison et al. | 128/781 |
| 4,802,494 | 2/1989 | Gardiner | 128/779 |
| 4,805,637 | 2/1989 | Walthert | 128/774 |
| 4,839,809 | 6/1989 | Leighton et al. | 364/413.02 |
| 4,846,194 | 7/1989 | Sabia | 128/781 |
| 4,871,998 | 10/1989 | Chaillou | 340/573 |
| 4,872,268 | 10/1989 | Perrault | 33/512 |
| 4,928,709 | 5/1990 | Allison et al. | 128/782 |

FOREIGN PATENT DOCUMENTS

| | | | |
|---|---|---|---|
| 3525756 | 12/1986 | Fed. Rep. of Germany | 128/781 |
| 1103849 | 7/1984 | U.S.S.R. | 128/781 |
| 1326244 | 7/1987 | U.S.S.R. | 128/781 |

OTHER PUBLICATIONS

Article entitled "Use of Noninvasive Techniques for Quantification of Spinal Range-of-Motion in Normal Subjects and Chronic Low-Back Dysfunction Patients" by Tom G. Mayer, M.D., et al, *Spine*, vol. 9, No. 6, 1984.

Article entitled "Effects of Prone Spinal Extension Exercise on Passive Lumbar Extension Range of Motion", by Richard L. Smith et al., *Physical Therapy* vol. 67, No. 10, Oct. 1987.

Primary Examiner—Max Hindenburg
Assistant Examiner—Guy V. Tucker
Attorney, Agent, or Firm—Kinney & Lange

[57] ABSTRACT

An apparatus for measuring the range of angular body motion about at least one axis of rotation. The apparatus includes a base with a first portion having means for engaging the body to provide a first reference point for measurement. A second portion of the base extends outward from the body generally perpendicular to the axis of rotation. A measurement member is positioned adjacent to the second portion of the base and is rotatably mounted to the base at the first reference point. The measurement member moves relative to the second portion of the base as the measurement member is pivoted about the axis of rotation. A slide arm is slidably mounted on the measurement member for sliding movement along a line substantially parallel to the plane of rotation of the measurement member. The slide arm has an outer end which is spaced from the measurement member and engages the body at a second reference point on an opposite side of the axis from the first reference point and there is measurable pivotal movement of the measurement member as the body is moved about the axis of rotation. A second portion of the apparatus uses angle indicators for measuring rotations of the spine about an upright axis and side to side pivotal movement.

19 Claims, 6 Drawing Sheets

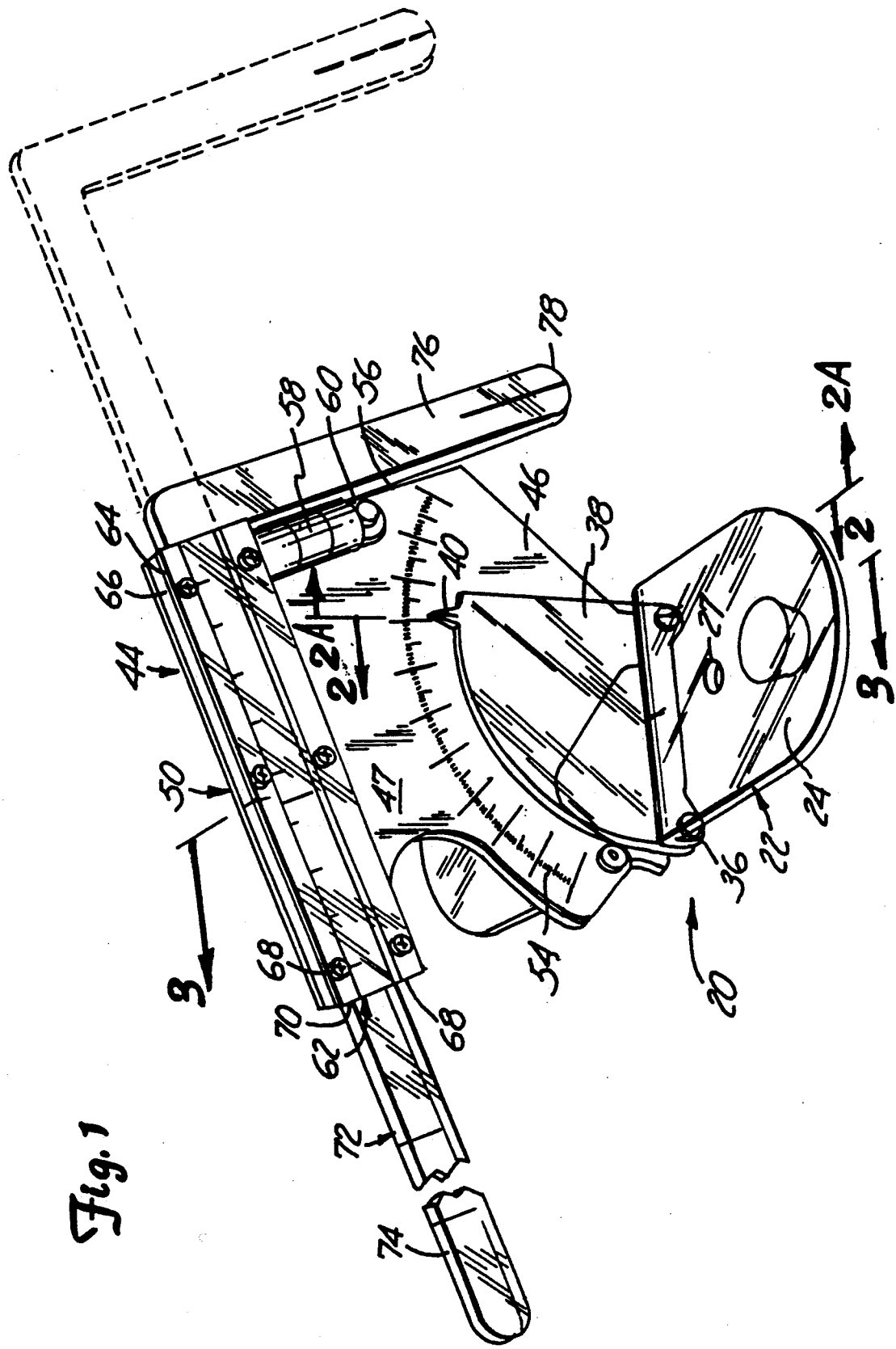

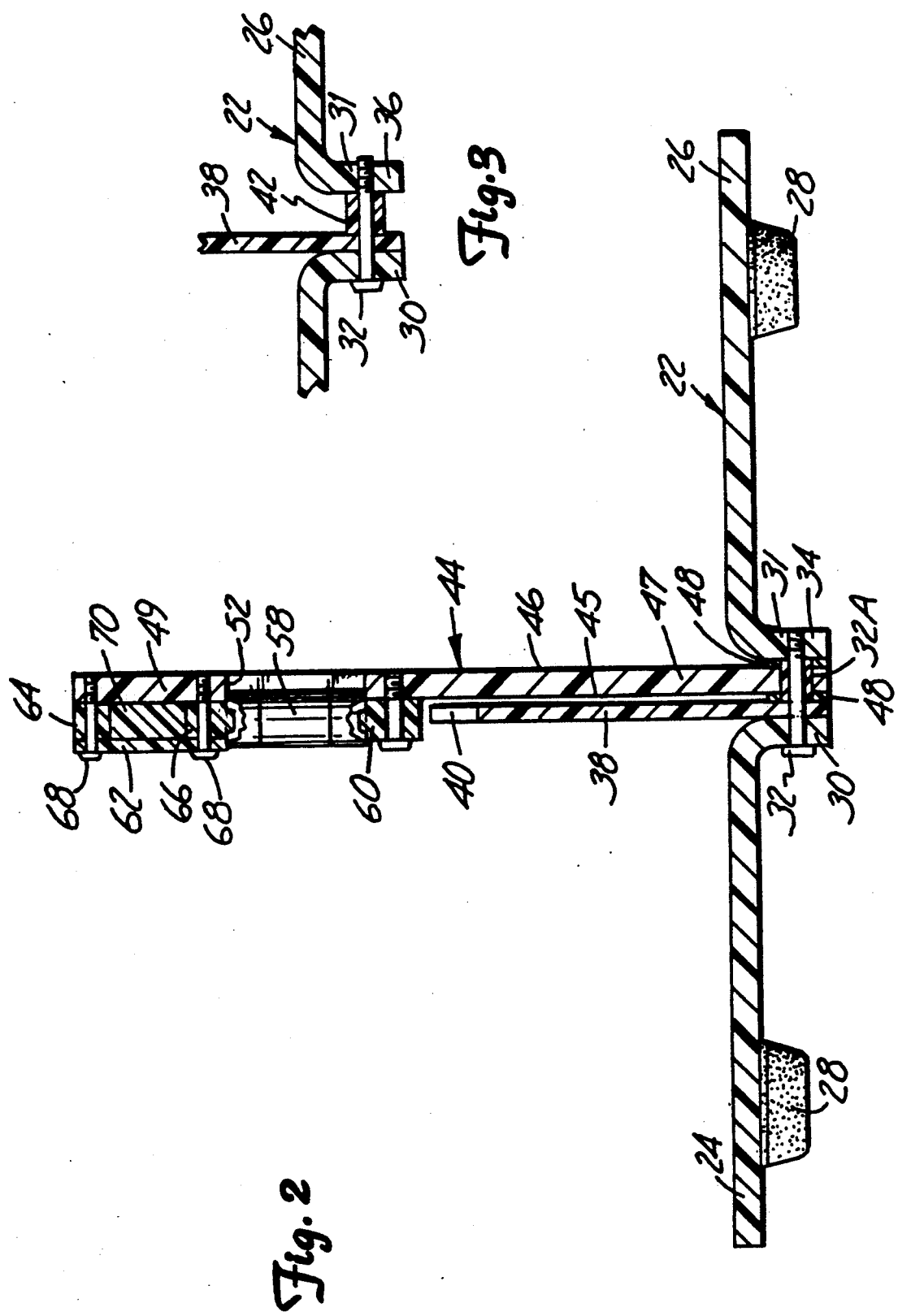

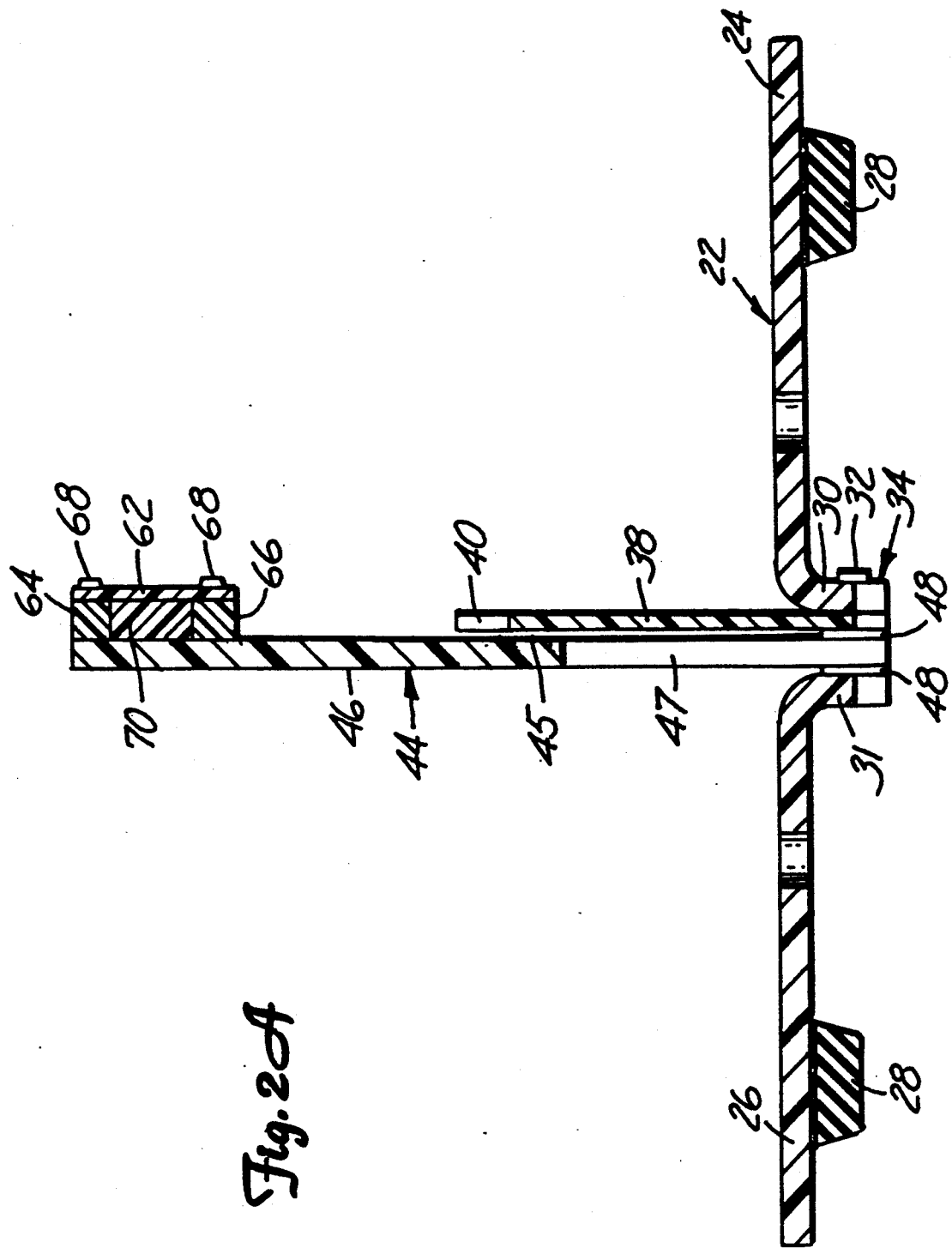

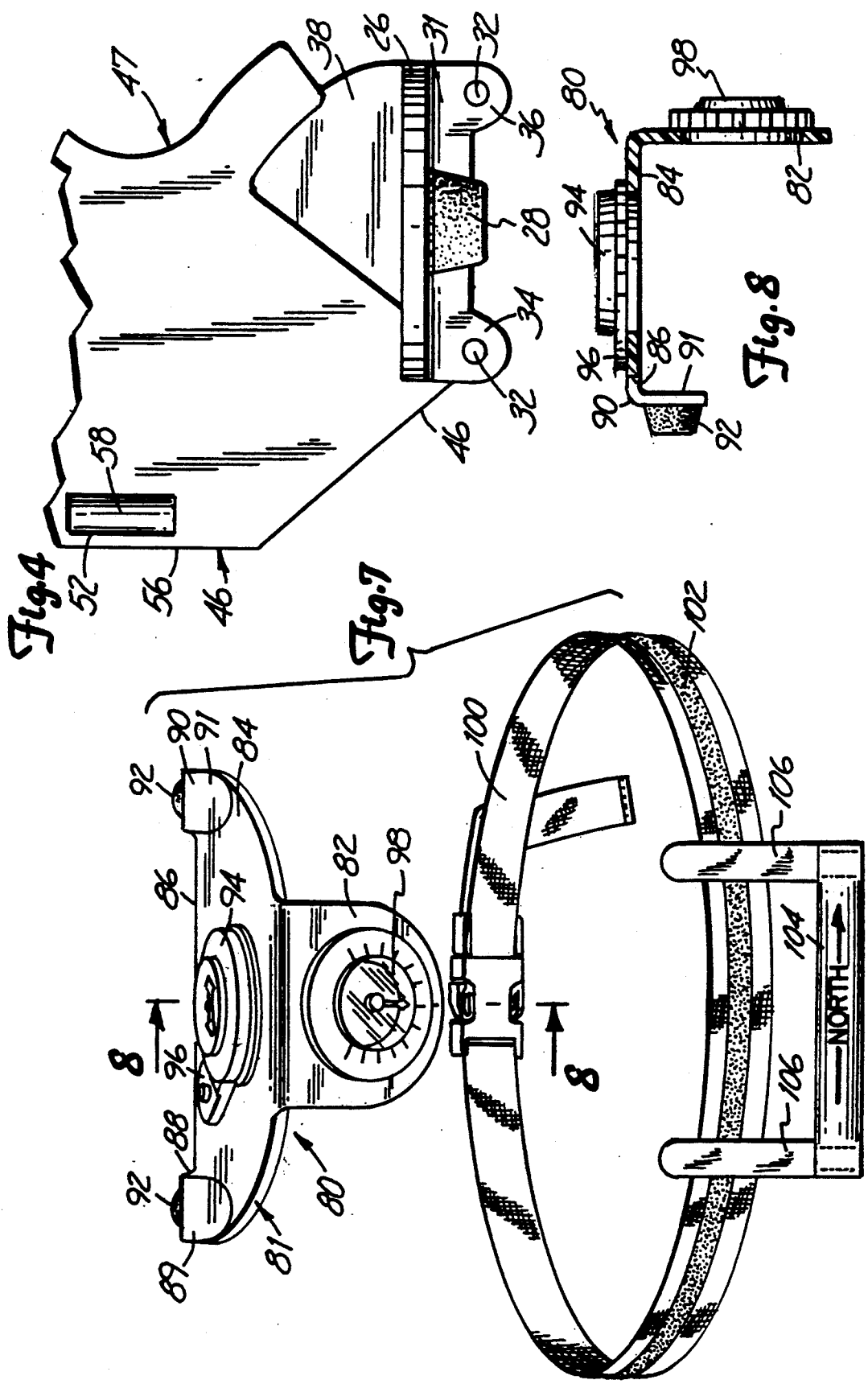

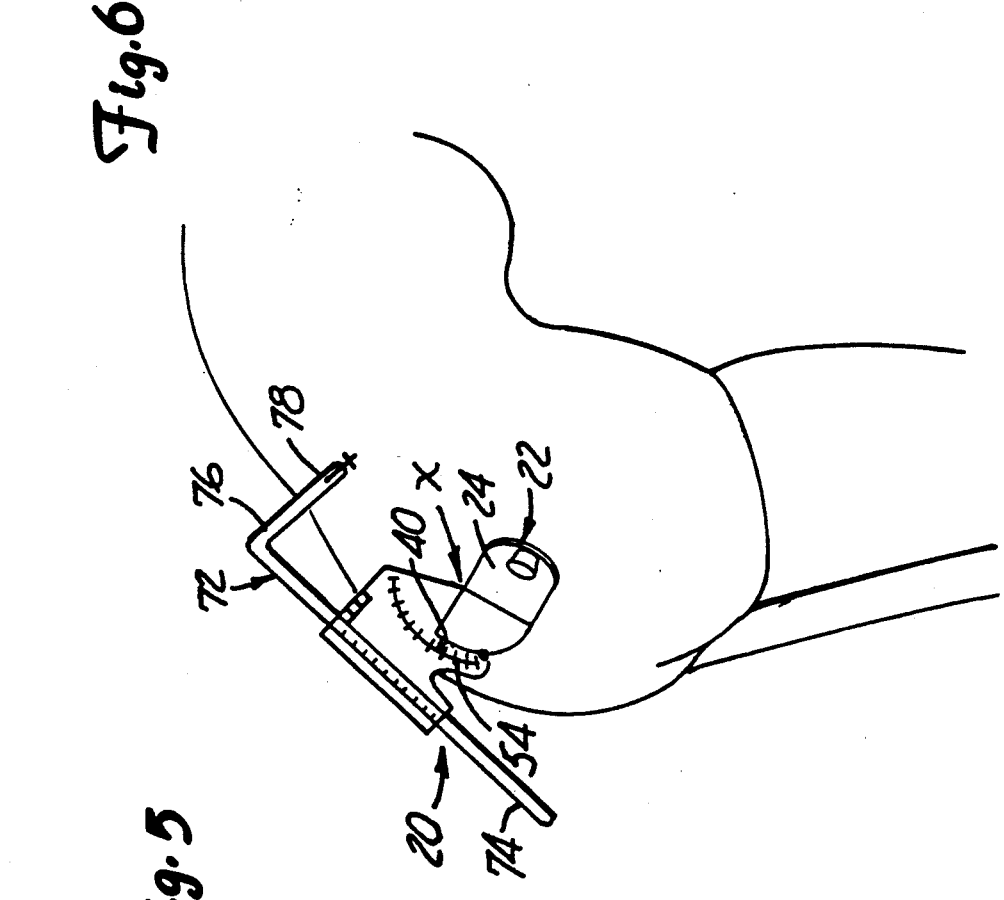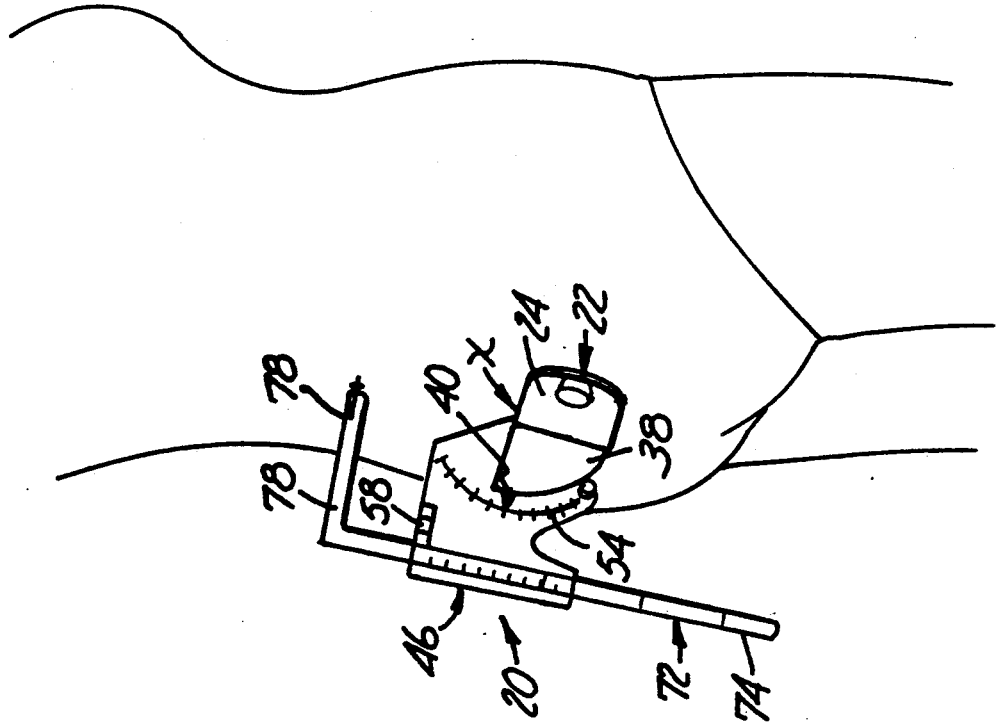

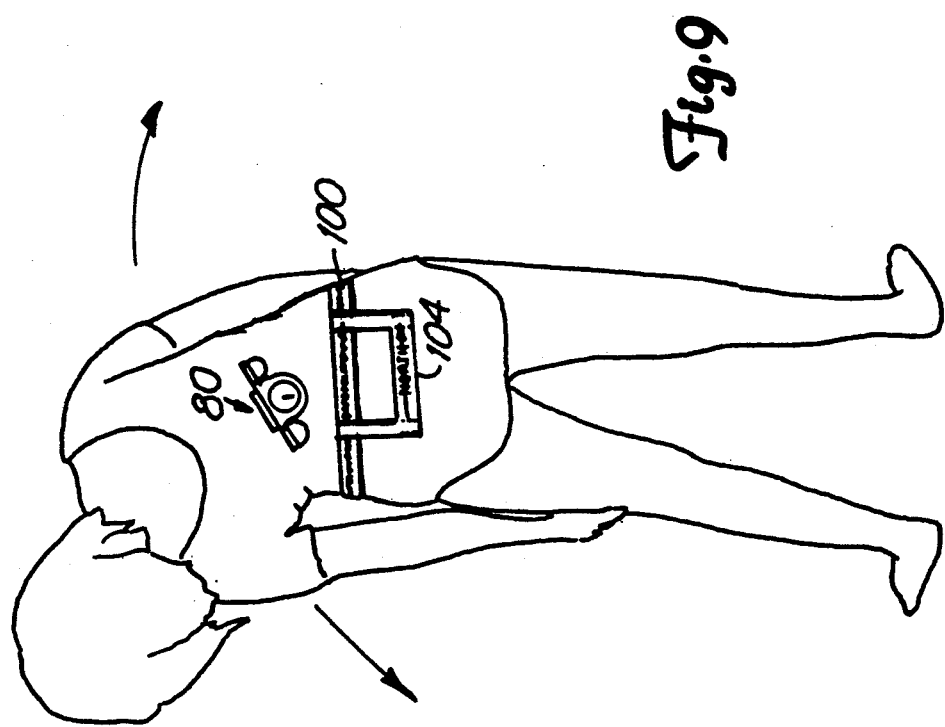
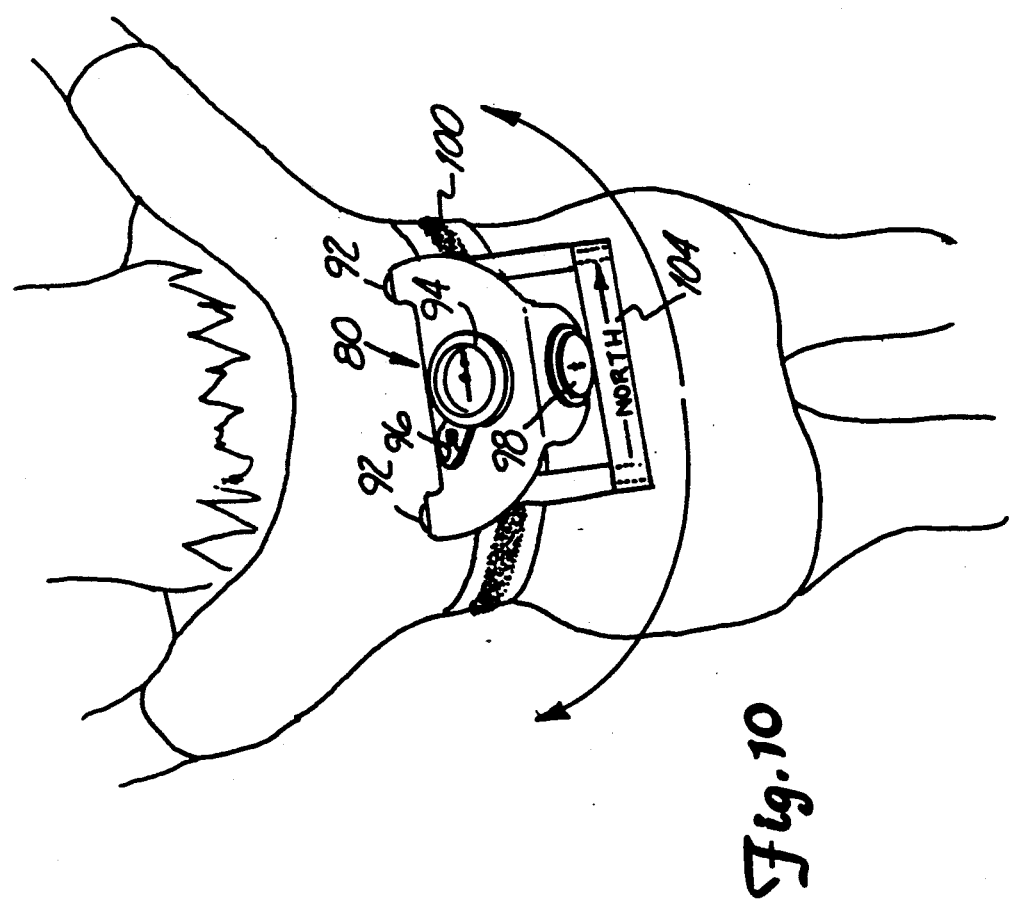

RANGE OF MOTION INSTRUMENTS FOR THE SPINE

BACKGROUND OF THE INVENTION

1. Field of the Invention

The present invention relates to devices that measure the motion of one human body part relative to another. In particular, the present invention relates to an apparatus for measuring the range of angular body motion about at least one axis of rotation.

2. Description of the Prior Art

Measuring the motion of a portion of a human body relative to another has been done utilizing compass-type angle indicators and pendulum-type inclinometers. Caliper-type devices, such as a spondylometer, used in combination with a protractor, also have been used to measure the motion of the thoracic and lumbar spine relative to the sacrum. However, the development of devices which are removably and stably mountable to the spine or other human body parts, and that do not require any repositioning of the device during the measurement process, while yielding accurate, verifiable, and reproducible data has not been accomplished by the prior art.

U.S. Pat. No. 2,532,915 discloses a device for determining the relative displacement of vertebrae through auditory signal analysis. The device uses a compass and a bubble level to orient the device and applies auditory signals to be transmitted through the vertebrae column and received by sound receivers.

U.S. Pat. Nos. 3,921,620, 3,943,912, and 4,587,956 disclose devices which comprise a magnetic body attached to a belt which is wrappable about the human torso or other body limb. The devices provide a magnetic field which is used to apply a magnetic flux to the human body for therapeutic purposes.

U.S. Pat. No. 4,108,164 discloses a device that measures flexural movement of the human torso. The device has a jacket with an angle sensing means, whose output is sensed by an electrical measurement device and which measures the angle of tilt of portions of the spine during the human act of leaning. U.S. Pat. No. 4,444,204 discloses a device for measuring scoliosis. The device is comprised of a frame with several laterally spaced parallel finger-like members situated to mimic the lateral curvature of the spine.

U.S. Pat. No. 4,485,825 discloses an instrument for measuring the positions and relative displacements of portions of the human body, including joints and the spinal column. The device uses a belt or suction cup to mount the instrument to the human body. The instrument includes a pendulum-type inclinometer and a compass-type angle indicator. To measure the motion of a body part relative to another, one instrument is placed on each of the cooperable body parts. Then compass and inclinometer readings are taken from each instrument before and after a controlled movement of a body part. The data is compared to measure the relative displacement of body parts. The device is also capable of measuring rotation of the spinal column by manipulating the compass device to a horizontal plane. This instrument is usable in a range of motion measurement method, such as the two inclinometer technique as disclosed in an article by Mayer et al., in SPINE, Vol. 9, No. 6, 1984.

U.S. Pat. No. 4,655,227 discloses a device used to determine mechanical injuries of the spine. The device is comprised of a computerized system whereby a mathematical model of a spine applicable to the five lumbar vertebrae and their respective structures, is compared to the actual movement of the spine measured by the use of a camera and an associated computer program.

U.S. Pat. No. 4,665,928 discloses a device used to measure the range of motion of multiple body parts relative to one another. The device is comprised of several pendulum-type electronic goniometers which are mounted to belts circumferentially wrappable about a human body part. The measurement output of the goniometers is read by a computer, which analyzes and compares the relative readings of the goniometers to determine the range of motion for a body part relative to another.

U.S. Pat. No. 4,730,625 discloses a device for monitoring the posture of a human and includes a shirt worn by the subject with an electronic sensor connected to a resistive element on the shirt. Upon a change in posture, the resistance of the element changes and the sensor indicates that a change in posture has occurred.

U.S. Pat. No. 4,777,965 discloses a device for measuring the range of motion for the cervical spine about three axis of rotation. The device utilizes a common eye-glass frame releasably securable on a human subject by means of nose pads and ear pieces. The device includes a pendulum-type angle finder situated about a horizontal axis and a compass-type angle finder situated about a vertical axis such that the two angle finders are mutually perpendicular to each other. The pendulum-type angle finder and compass are rotatable 90 degrees to permit tri-planar angle measurements of the cervical spine.

U.S. Pat. No. 4,839,809 discloses a device for measuring human ambulatory turning behavior. The device includes a compass means which generate electronic signals thereby indicating the degree and direction of ambulatory rotational movement of the subject.

Thus, the use of compass-type devices, pendulum-type devices, and caliper-type devices have been used to measure the motion of one body part relative to another. In particular, spinal range of motion has been measured for flexion and extension relative to the sacrum, as well as lateral bending and rotation of the spine in the pelvic area.

However, these devices generate a variety of errors within the measurement method. For example, in spinal measurements the inclinometer-type device may rock on the sacrum or on measurement points located on the human torso. Likewise, if the single inclinometer technique is used, then the inclinometer must be repositioned several times to measure range of motion for both flexion and extension. This repositioning introduces measurement errors because of shifting reference points. Another significant problem is relocating the prior measurement point or location on a human torso if a range of motion test is desired to be replicated at a subsequent testing period. The single or double inclinometer technique also presents difficulties in distinguishing pelvic motion from torso motion. Rotation measurements of the torso using a singular compass-type device also have been plagued with measurement errors because it is difficult to isolate true torso rotation from unwanted pelvic rotation.

There is a continuing need for an improved device measuring the range of motion for body parts. The device should be designed in such a manner that it is removably mountable to the spine or body part in a stable fashion to minimize rocking of the device on the measurement locations, thereby permitting the measurement of reproducible and verifiable data. The device should be of a simple, lightweight, mechanical design.

SUMMARY OF THE INVENTION

The present invention is an apparatus for measuring the range of angular body motion about an axis of rotation. The apparatus includes a base having a first portion with means for engaging the body to provide a first reference point for measurement. The base has a second portion extending outward from the body generally perpendicular to the axis of rotation. A measurement member is positioned adjacent to the second portion of the base and is rotatably mounted to the base at the first reference point. The measurement member pivotally moves relative to the second portion of the base. The pivot axis of the measurement member is close to the body axis of rotation when in use. A slide arm is slidably mounted on the measurement member for sliding movement in directions along a line parallel to the plane of pivotal rotation of the measurement member. The slide arm has an outer end that is spaced from the measurement member for engaging the body at a second reference point on an opposite side of the pivot axis of the measurement member from the first reference point. The outer end moves as the body is moved about the body axis to cause pivotal movement of the measurement member relative to the first portion of the base. The apparatus includes a means for determining the amount of pivotal movement of the measurement member relative to the second portion of the base.

In a preferred embodiment of the present invention, the means for engaging the body to provide a first reference point comprises a plurality of protrusions for engaging the human body aligned on an edge of the first portion of the base and which are substantially perpendicular to the axis of rotation. The means for engaging the body comprises a base having a pair of wings extending laterally outward in both directions from and generally perpendicular to the second portion of the base and each wing has at least one pad for releasably engaging the human body adjacent the first reference point.

As part of an overall measurement system of the present invention, the measuring apparatus comprises a second frame having an elongated base with protrusions for resting on opposite sides of the spine of a subject. The frame includes a pair of angle finders positioned thereon to measure rotation and flexion angles about mutually perpendicular axes, wherein one of the angle finders is a magnetic compass.

BRIEF DESCRIPTION OF THE DRAWINGS

FIG. 1 is a perspective view of a first range of motion instrument for the spine incorporating the present invention.

FIG. 2 is a sectional view taken along line 2—2 of FIG. 1.

FIG. 2A is a sectional view taken along line 2A—2A of FIG. 1.

FIG. 3 is a fragmentary sectional view of the present invention taken along a line 3—3 of FIG. 1.

FIG. 4 is a side elevational view of the device of FIG. 1, as seen from an opposite side from that shown in FIG. 1.

FIG. 5 is a perspective view of the device of FIG. 1 in position on a torso of a human subject.

FIG. 6 is a perspective view similar to FIG. 5 with the human subject positioned in spinal flexion.

FIG. 7 is a perspective view of a second device used in a system of angle measurements according to the present invention.

FIG. 8 is a sectional view of the second device taken along line 8—8 as seen in FIG. 7.

FIG. 9 is a perspective view of the second device shown in FIG. 7 positioned on a torso of a human subject who is in lateral flexion.

FIG. 10 is a perspective view of the second device shown in FIG. 7 in position on a torso of a human subject whose torso is rotated.

DETAILED DESCRIPTION OF THE PREFERRED EMBODIMENTS

A first motion analyzer for measuring the degree of spinal flexion and extension, according to the present invention, is illustrated generally at 20 in FIG. 1. As can be seen in FIGS. 1-4, the first motion analyzer 20 has a base 22 with a first wing 24 and a second wing 26 extending outwardly from an upright, platelike support body 38. The wings form a first base portion and are fixed to and support the upright body 38 which forms a second base portion. FIG. 4 shows the side of the first motion analyzer 20 opposite from that seen in FIGS. 1, 5 and 6. Each wing 24 and 26 has a body contact pad 28 near its remote end and the first wing 24 has a flange 30 and the second wing 26 has a flange 31 which are used to support the upright body 38.

A pair of locator apertures 27 are defined on the base 22, one on each of the respective first and second wings 24 and 26. The locator apertures 27 are used to aid the positioning of the base 22 relative to a body on which the base 22 is supported during use. The apertures are centered between feet 34 and 36, so when an operator presses a forefinger and thumb on the apertures, the load is substantially equal on each of the feet 34 and 36 to insure these.

A pair of studs 32 cooperate with and extend through the flanges 30 and 31 of the wings and the studs also pass through the support body 38, and suitable spacers to join the two wings together and form the base 22. As best shown in FIG. 4, the flanges 30 and 31 of the first wing 24 each have an aligning or mounting end portion forming a first foot 34 at a first end of the base 22 and second foot 36 at a second end of the base 22.

The first foot 34 and the second foot 36 act to establish and maintain point or small area contact with a body of a human subject, thereby stabilizing the base 22 on the body of the subject, particularly when compression loads are applied at the locating apertures 27. When in contact with the body, the feet 34 and 36 define a first reference location on the body. The pads 28 on the wings 24 and 26 also contact the body of the subject at laterally spaced locations to maintain the position of the feet 34 and 36 and the base 22 relative to the body. Each pad 28 is positioned on an underside of the respective wings and preferably is made of an elastomeric material. The wings 24 and 26 preferably are made of a plastic material, which may be transparent.

As best shown in FIGS. 1 and 2, the upright body 38 is a flat plate and a reference pointer 40 is formed thereon. The pointer 40 has a center line marked thereon to designate a reference point. The upright body 38 is positioned between the flanges 30 and 31 of the wings 24 and 26, and, as stated, is secured between the flanges by the studs 32. The upright body 38 extends upward from the base 22 substantially perpendicular to the planes of the wings 24 and 26. As best shown in FIGS. 2 and 3, the upright body 38 is clamped in position against the flange 30 and flange 31 using a sleeve type spacer 42. The upright body 38 preferably is made of a plastic material, which may be transparent.

As best shown in FIGS. 2 and 4, a measurement frame 44 also is a flat plate of plastic formed to have a neck portion 47 and a measurement portion 49, and a first side 45 and a second side 46. The neck portion 47 is pivotally mounted to the base 22 between the upright body 38 and the flange 31 of the second wing 26. The neck portion 47 is held in position by one stud 32 which extends through a spacer 32A to clamp the flanges 30 and 31 together. The neck portion 47 and the upright body 38 are pivotally mounted on the spacer 32A on the one stud 32. A pair of annular discs 48 are positioned on the spacer over stud 32 on opposite sides of the neck portion 47 to properly position the frame 44 and provide friction drag on the frame 44. One of the disks 48 is positioned between the upright body 38 and the neck portion 47 and the other disk 48 is positioned between the neck portion 47 and the flange 31 of the second wing 26. The neck portion 47 is pivotable about the axis of the one stud 32 and the frame 44 can be moved in a plane of rotation about the axis of stud 32. The pivot axis is at the end of the base 22 where the first foot 34 is located.

A rectangular window aperture 52 is defined on the measurement portion 49 of the frame 44 adjacent to an edge 56 of the frame 44. A bubble level 58 is mounted on the first side 45 of the frame 44 such that the bubble level 58 is visible through the window aperture 52 when the first motion analyzer 20 is viewed from the second side 46 of the frame 44 (as seen FIG. 4). An ear 60 on the bubble level 58 is fastened to the frame 44 by a fastener to support the bubble level 58 in position.

Angle markings 54 are printed on the measurement frame 44 on an arc corresponding to the path in which the frame 44 moves past the pointer 40. Upon pivoting of the measurement frame 44 about the axis of the one stud 32, the reference pointer 40 will indicate the degree of pivotal movement of the frame 44 relative to the pointer 40 about the axis of rotation. As can be seen in FIGS. 1 and 2, a first top elongated spacer 64 and a second parallel elongated spacer 66 are positioned against the first side 45 of the frame. A transparent cover plate 62 is placed on the outside of the spacers 64 and 66 and a plurality of studs 68 hold the plate 62 and spacers in place to define a slide arm chamber 70. A linear reference scale is printed on side 45 of frame 44, and the scale is visible through plate 62. The slide arm chamber 70 extends the length of the measurement portion 49 of the frame 44. One of the fasteners for the second elongated spacer 66 is used to hold an ear of the bubble level 58 in position.

As seen in FIG. 1, a slide arm assembly 72 includes a slide portion 74, an extension or probe portion 76, which has an outer contact or control end 78. The slide portion 74 of the arm 72 extends through the slide arm chamber 70 and is slidably movable therethrough longitudinally relative to the frame 44. The extension or probe portion 76 of the slide arm 72 is generally perpendicular to the slide portion 74 and is aligned generally parallel to the edge 56 of frame 44. The contact end 78 is used for contacting the body of the subject at a second reference location on the subject.

The slide arm 72 preferably is a transparent plastic and has graduated linear markings along the slide portion 74 that are cooperable with the linear reference scale on side 45 of frame 44 to indicate the position of the slide portion 74 of slide arm 72 relative to the frame. The scale indicates the distance from the center of foot 34 to the center of control end 78. Use of this reference scale permits finding the second reference location for control end 78 at a subsequent measurement session after the first reference location for the center of foot 34, right at the top of the sacrum (S1) has been reestablished. The slide arm 72 is removable from the sleeve assembly 62 and may be exchanged for slide arms having slide portions 74 of different length. The slide arm 72 is shown in phantom in FIG. 1 illustrating the extension of the slide arm 72 through the slide arm chamber 70.

In use, as best shown in FIGS. 5 and 6, the analyzer 20 is mounted on a posterior of the body of the human subject at the rear overlying the base of the spine. The base 22 is positioned so that the first foot 34 contacts the top of the sacrum (S1) of the subject to designate the first reference location of measurement. The second foot 36 will rest on the lower portion of the sacrum and the feet 34 and 36 are aligned in a plane parallel to the midsagittal plane of the subject. The first wing 24 and the second wing 26 extend laterally on opposite sides of the spine. An operator utilizes the finger apertures 27 to apply compression force to hold the wings 24 and 26 in position on the buttock region to maintain equal pressure on each foot 34 and 36 for stability to eliminate any rocking motion and provide a stable platform for measurements. The feet 34 and 36 are in contact with the sacrum. The pads 28 of the respective wings 24 and 26 engage the top part of the buttock to further stabilize the base 22 and maintain contact of the feet 34 and 36 with the sacrum. The operator preferably marks the top of the sacrum (S1) on the subject for accurate remeasurements during the same session. Most operators can repeatedly place foot 34 at S1 for subsequent sessions Next, while maintaining the base 22 in the desired position relative to the sacrum, the operator grasps slide arm 72 near the contact end 78 of the extension portion 76 and moves the slide arm 72 through the slide arm chamber 70 to position the contact end 78 at a desired location on the spine of the subject The operator, as an example, locates the twelfth torso vertebra (commonly and hereinafter referred as "T12") on the spine of the subject and marks this location, thereby defining the second reference location of measurement. When the slide arm 72 is manipulated such that contact end 78 contacts the spine at T12, the first motion analyzer 20 is established in contact with designated portions of the human subject.

With the operator maintaining firm contact between the contact end 78 and T12, and between the feet 34 and 36 and the sacrum, the subject moves the torso into spinal flexion. During the movement of T12 as the subject bends about the axis of rotation, the extension portion 74 of the slide arm 72 may extend or slide along the spacers defining the slide arm chamber 70 and causes the measurement frame 44 to pivot relative to the body 38 such that the angle markings 54 move relative to the reference pointer 40 to indicate the relative degree of spinal motion in flexion about the body axis of rotation. The operator notes this positioning of the angle markings or scale 54 relative to the reference pointer 40. Next, while the operator maintains the first motion analyzer 20 in position at the first and second reference locations, the subject returns to a normal posture from full flexion The positioning of the angle markings 54 relative to the reference pointer 40 is compared to the initial positioning of the angle markings or scale 54 relative to the pointer 40 to determine if the first protrusion 34 of the base 22 has shifted relative to the sacrum during the measurement process. Likewise, the operator compares the positioning of the slide portion 74 relative to the linear reference scale on the side 45 of frame 44 and compares it with its initial positioning to determine if the contact end 78 has shifted relative to T12 during the measurement process. The readings taken are recorded for future sessions, as desired.

The device is used in a similar fashion to measure the range of spinal motion during spinal extension of the subject by initially positioning the device on the sacrum S1 and the T12 vertebra of the subject. The arm 72 moves parallel to the line between S1 and T12. Once again, the contact end 78 is held in contact with T12 and the first foot 34 is maintained in contact with the sacrum as the subject moves its torso into extension relative to the pelvic area.

The relative pelvic tilt to the vertical is measured by utilizing the bubble level 58 positioned on the measurement frame 44. The operator positions the base 22 relative to the sacrum as described above, and then pivots the measurement frame 44 downwardly relative to the pointer body 38 until the bubble level 58 indicates a level plane. The angular reading is recorded and the frame can be removed.

The first motion analyzer 20 of the present invention has significant advantages over the prior art. Once the first motion analyzer 20 is mounted on the desired locations of the human subject, the first motion analyzer 20 need not be repositioned during the measurement process and thus eliminates the repositioning errors associated with the relocation of measurement devices relative to the body during the measurement process. Ordinarily, in the single inclinometer technique, the inclinometer would have to be repositioned four times to measure both flexion and extension. The double inclinometer method is simpler than the single inclinometer technique but also has shortcomings because there is difficulty in minimizing rocking of the inclinometer on the sacrum or the T12 measurement point during the technique. Another difficulty of the double inclinometer technique stems from the difficulty of relocating the second reference location relative to the first reference location at a subsequent measurement session.

The analyzer 20 of the present invention reduces measurement errors in several ways not utilized by the prior art. The base 22 with wings 24 and 26 and their respective pads 28 minimize movement of the base 22 on the sacrum. The first foot 34 allows for precise location of the motion analyzer 20 on the desired reference locations such as the top of the sacrum S1 and other bony structures. Furthermore, the use of the contact end 78 (which provides point contact) of the slide arm 72 in combination with the measurement frame 44 provides stability and diminishes the problem of rocking of an individual measurement device on the desired reference location such as T12. Another advantage is the ability to measure the positioning of the slide arm 72 relative to the measurement frame 44 to allow for subsequent accurate relocation of the second reference location, such as T12, relative to the sacrum (S1), thus permitting replication of earlier measurement sessions. This gives an identical segment of the spine to be measured every time. Of course, the device also may be suitably adapted to measure the motion of body parts other than the spine relative to other body parts about an axis of rotation.

A second motion analyzer for measuring the degree of rotational and lateral flexion of the present invention is illustrated generally at 80 in FIGS. 7 and 8. The second motion analyzer 80 includes a frame 81 with a first plate 82 and a second plate 84 having an edge 86. A first protrusion 88 and a second protrusion 90 are spaced from each other and defined on opposite ends of the edge 86 and extend outward therefrom. A first lip 89 is defined on the first protrusion 88 and a second lip 91 is defined on the second protrusion 90. Each lip has at least one pad 92. A first angle indicator 94 has a mounting plate 96 and is positioned on the second plate 84. A second angle indicator 98 is positioned on the first plate 82.

The first plate 82 is positioned generally perpendicular to the second plate 84 such that the first angle indicator 94 is positioned substantially perpendicular to the second angle indicator 98. The first angle indicator 94 preferably is a magnetic compass and the second angle indicator 98 preferably is a vertical inclinometer-type device. When the frame 81 is rotated about axis which is generally parallel to the axis of the first angle indicator 94, the first angle indicator 94 indicates the degree of rotational movement of the frame 81 When the frame 81 is rotated about an axis which is generally parallel to the axis of the second angle indicator 98, the second indicator 98 indicates the degree of tilt or vertical angle change of the frame 81 relative to a generally vertical plane.

The first protrusion 88 and the second protrusion 90 extend outward from the frame 81 such that the lips 89 and 91 are spaced from the edge 86 and generally parallel thereto. The pads 92 are mounted on the first and second lips 89 and 91, respectively. The frame 81 is maneuverable such that the pads 92 of the first and second protrusions 88 and 90 contact the human torso on laterally opposite sides of the spine of the human subject. The examiner can provide the pressure on each of the pads to stably mount the frame 81 to the torso of the subject and the examiner's fingers can grasp the respective sides of the rib cage for firm support. The edge 86 is generally then perpendicular to the midsagittal plane of the subject.

A belt 100 having a fastener 102, which is positioned along the length of the belt 100, is shown in FIG. 7. An elongated magnetic body 104 having a pair of straps 106 is shown secured to the belt 100 by the cooperation of the straps 106 with the fastener 102. The belt preferably is of a size for wrapping about the human torso of a subject and for securing thereon. Thus, as shown in FIGS. 9 and 10, the magnetic body 104 is positioned adjacent to the pelvic area of the human subject. The magnetic body 104 provides a local magnetic field independent of that of the earth's magnetic field adjacent to the pelvic area and torso to provide a magnetic field of reference for the compasstype first angle indicator 94.

As can be seen in FIGS. 9 and 10, the second motion analyzer 80 is shown applied to and cooperating with the torso of the human subject. In FIG. 9, the unit 80 is being used to measure the degree of lateral flexion of the human torso about an axis of rotation. A reference location, such as T12, is located along the spine of the subject. Next, the operator grasps the frame 81 adjacent to the lips 89 and 91, respectively, and mounts the frame 81 to the human torso such that the edge 86 is adjacent to and spaced from the reference location and the pads 92 of their respective lips 89 and 91 are positioned laterally on opposite sides of the spine at T12. The frame 81 is maneuvered until the second angle indicator 94 reads zero to indicate that the frame 81 is in a substantially horizontal plane or generally perpendicular to the midsagittal plane of the subject. While the operator holds the pads 92 of the frame 81 in firm contact with the back of the rib cage of the human torso (with the thumbs on the respective pads and the fingers gripping around the sides of the rib cage), the subject moves into lateral flexion to the left or right side as directed. The second angle indicator 98 indicates the change in position of T12 relative to the midsagittal plane during lateral flexion. Finally, the subject moves its torso to the upright position when the second angle indicator 98 reads zero.

As can be seen in FIG. 10, the second motion analyzer 80 is used to measure the rotation of the human torso relative to the controlled position of a sacrum or pelvic area about a generally upright axis and from side to sides (lateral flexion). The belt 100 is secured about the human torso and the magnetic body 104 is attached to the belt by fastening the straps 106 to the fastener 102 such that the magnetic body 104 is positioned across S1 and horizontally. The patient is positioned so that the arrow on the magnet body points north. Next, the frame 81 is mounted to the human torso by forcing contact of the pads 92 of their respective lips 89 and 91 into engagement with the human torso on laterally opposite sides of the spine at the T12 reference point such that the first angle indicator 94 is positioned adjacent the magnetic body 104. The compass ring is moved to zero, the reading at this stage. That is the ring that is moved so the zero mark is aligned with the compass needle. The frame 81 and the pads 92 are held firmly in contact with the human torso as the subject rotates its torso relative to the pelvic region. The first angle indicator 94 indicates the degree of torsional rotation relative to the pelvic area about an upright axis. Likewise, a similar measurement may be taken for rotation of the human torso about the sacrum region in a subject-orientated right direction.

The second motion analyzer 80 of the present invention has considerable advantages over the prior art. First, when used for lateral flexion measurements, single inclinometer devices typically are mounted directly at the spine and thus suffer from a less accurate mounting of the device to tract lateral flexion of the torso. The present invention, however, has an elongated edge 86 with the extending protrusions 88 and 90 such that the inclinometer-type second angle indicator 98 is accurately oriented relative to the midsagittal plane and this orientation is maintained by the operator or examiner holding the unit in place, as described, during lateral flexion (side to side) of the torso resulting in more accurate tracking of lateral flexion. Other problems associated with the use of devices in the prior art include an inability to isolate true human torsional rotation from undesired rotation of the pelvic area. The present invention solves this problem by utilizing a magnetic body 104 associated with the first compass-type angle indicator 94 to provide an independent magnetic field so all measurements with indicator 94 are made relative to the magnet body. The arrangement thereby compensates for unwanted pelvic rotation and provide the operator with the true and accurate degree of human torsional rotation.

The first and second motion analyzers together form a kit used for reliably examining the bending and rotational movements of the spine of a patient.

Although the present invention has been described with reference to preferred embodiments, workers skilled in the art will recognize that changes may be made in form and detail without departing from the spirit and scope of the invention.

What is claimed is:

1. An apparatus for measuring a range of angular body motion including:
   a base having a first portion with means for engaging a body of a subject providing a first reference point for measurement, and a second portion extending outward from the first portion generally perpendicular to an axis of rotation;
   a measurement member adjacent to the second portion of the base rotatably mounted to the base at the first reference point, the measurement member moving in a plane of rotation relative to the second portion of the base as the measurement member is pivoted about the axis;
   a slide arm slidably mounted on the measurement member for sliding movement along a plane substantially parallel to the plane of rotation of the measurement member and having an outer end slidably movable to positions spaced from the measurement member for engaging a body engaged by the base at a second reference point on an opposite side of the axis from the first reference point to cause pivotal movement of the measurement member as the body is moved through an angular range of motion; and
   means for determining the amount of pivotal movement of the measurement member relative to the second portion of the base.

2. The apparatus of claim 1 wherein the means for engaging the body further includes:
   a plurality of protrusions on the base for engaging the body on a line substantially perpendicular to the axis of rotation.

3. The apparatus of claim 1 wherein the means for engaging the body further include:
   a pair of wings extending oppositely outward from and generally perpendicular to the second portion of the base.

4. The apparatus of claim 3 wherein the wings further include:
   a plurality of pads positioned along a line adjacent to the first reference point for releasably engaging the body of a subject to stabilize the apparatus on the body.

5. The apparatus of claim 1 wherein the outer end of the slide arm further includes:
   an extension arm extending outward from and generally perpendicular to the slide arm to engage the body at the second reference point.

6. The apparatus of claim 1 wherein the measurement member further includes:
   a bubble level positioned on the member for determining the amount of tilt during angular motion.

7. The apparatus of claim 1 wherein the means for determining the amount of pivotal movement of the member further includes:

a first part cooperate with a second part to indicate the degree of pivotal movement.

8. The apparatus of claim 7 wherein the first part is a reference mark and the second part is a protractor.

9. The apparatus of claim 7 wherein the first part is positioned on the second portion of the base and the second part is positioned on the measurement member.

10. An apparatus for measuring the range of motion for a spine, including:
a frame, including:
a base having a first portion with at least two protrusions defined thereon for engaging a body of a subject having a spine to provide a first reference location along a longitudinal axis of the spine of such body, the base having a second portion positioned substantially perpendicular to said first portion and providing a reference pointer, the base also having means for supporting the base extending outwardly in opposite directions from an generally perpendicular to the second portion, and having means for releasably engaging the body connected to the means for supporting the base;
a member adjacent to the second portion of the base, the member being rotatably mounted to the base, and having an angular movement indicator associated with the reference pointer to indicate the amount of pivotal movement of the member relative to the reference pointer, a housing on the member and having a slide in a plane parallel with the second portion of the base, and a bubble level on the member to indicate pelvic tilt; and
a slide arm slidably extending through the housing and having a body contact portion extending outward from and generally perpendicular to the slide arm for engaging the body of the subject to provide a second reference location and to cause pivotal movement of the member as the spine of the subject is moved about the axis.

11. The apparatus of claim 10 wherein the angular movement indicator is a protractor.

12. The apparatus of claim 10 combined to form a kit including a second frame having an elongated base having spaced protrusions for resting on opposite sides of the spine of a subject and having a pair of angle finders thereon which measure angles about mutually perpendicular axes, one of the angle finders comprising a magnetic compass.

13. The kit of claim 12 and further including:
a magnetic body detachably mounted to a belt circumferentially mountable about a torso of the subject, the magnetic body being selectively positionable to provide a field affecting the magnetic compass.

14. The kit of claim 12 wherein the second frame further includes:
a pair of plates, a first plate having the magnetic compass angle finder positioned thereon and a second plate cooperable with and generally perpendicular to the first plate with the other angle finder positioned thereon, the second plate being adjacent to the elongated base.

15. An apparatus for measuring the range of spinal motion of a human torso about at least two axes of rotation including:
a frame having a first plate having a surface and a second plate having a surface substantially perpendicular to the first plate surface, the second plate having at least a pair of protrusions extending outward from an edge of the second plate on opposite sides of a center axis thereof spaced apart to releasably engage a human torso at two locations defining a line parallel to the second plate surface, the protrusions being positionable on laterally opposite sides of the spine and contacting a back of a rib cage of the human torso above a pelvic area and below a shoulder area of the human torso;
at least two angle finder shaving axes which lie on a common plane with the axes of rotation, the first plate surface of the frame having an inclinometer angle finder positioned thereon and the second plate surface of the frame having a magnetic compass angle finder positioned thereon; and
an elongated magnetic body detachably mounted to a belt circumferentially mountable about the human torso, the magnetic body being selectively positionable below the belt and extending across the back of the human torso at substantially the level of the sacrum to provide a magnetic field that influences the magnetic compass angle finder when the frame is contacting the back of the human torso.

16. The apparatus of claim 15 wherein the magnetic body further includes:
securing means extending outward from the magnetic body which are cooperable with the belt.

17. The apparatus of claim 16 wherein the securing means is a pair of straps extending outward from the magnetic body.

18. A method for measuring the range of angular spinal motion about at least one axis of rotation comprising the steps of:
locating a first reference point on a body of a subject having a spine;
providing a frame having a base for engaging the body of the subject along the spine at the first reference point and stabilizing the base on the spine;
providing a pivoting member cooperable with the base to permit pivotal movement of the member relative to the base about the first reference point;
locating a second reference point on the body of the subject along the spine;
providing an arm cooperable with the pivoting member to permit slidable movement of the arm relative to the member along a plane parallel to the rotation of the member;
engaging the body of the subject along the spine at the second reference point on an opposite side of the axis from the first reference point with an outer end of the arm by manually holding the base thereto to cause pivotal movement of the member as the spine of the subject is moved about the axis;
moving the torso in flexion and then extension and gauging the amount of pivotal movement of the member relative to the reference frame to determine the amount of angular spinal motion in flexion and extension, respectively; and
disengaging the base and outer end from the body of the subject.

19. The method of claim 18 and further comprising the steps of:
locating a third reference point on the body of the subject along the spine;
providing a second frame for stably engaging the torso on opposite sides of the spine of the subject;
engaging the body of the subject at the third reference point by manually holding the second frame to the torso in a generally horizontal fashion;

providing a pair of angle finders positioned on the second frame, the angle finders oriented to indicate angles for movement about mutually perpendicular axes, with one of the angle finders being a magnetic compass and the other angle finder being an inclinometer;

moving the torso in lateral flexion and taking measurements with the inclinometer angle finder to determine the amount of angular spinal motion about the axis;

mounting a belt to the body of the subject by circumferentially wrapping the belt about the torso and positioning a magnetic body cooperable with the belt adjacent to and spaced from the magnetic compass angle finder;

rotating the torso about an axis generally parallel to the longitudinal axis of the spine and taking measurements of the magnetic compass angle finder to determine the amount of rotation.

* * * * *

UNITED STATES PATENT AND TRADEMARK OFFICE
CERTIFICATE OF CORRECTION

PATENT NO. : 5,188,121
DATED : February 23, 1993
INVENTOR(S) : GORDON N. HANSON It is certified that error appears in the above-identified patent and that said Letters Patent is hereby corrected as shown below:

Col. 11, line 1, delete "cooperate", insert --cooperable--

Col. 12, line 9, delete "finder shaving", insert --
--Finders having --.

Signed and Sealed this

Twenty-eighth Day of December, 1993

*Attest:*

BRUCE LEHMAN

*Attesting Officer*     *Commissioner of Patents and Trademarks*